United States Patent
Koide

(10) Patent No.: US 8,204,441 B2
(45) Date of Patent: Jun. 19, 2012

(54) TRANSMITTING APPARATUS, BODY-INSERTABLE APPARATUS, AND TRANSMITTING AND RECEIVING SYSTEM

(75) Inventor: Naoto Koide, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/116,193

(22) Filed: May 26, 2011

(65) Prior Publication Data

US 2011/0286536 A1    Nov. 24, 2011

Related U.S. Application Data

(63) Continuation of application No. PCT/JP2010/063550, filed on Aug. 10, 2010.

(30) Foreign Application Priority Data

Nov. 26, 2009   (JP) .................................. 2009-269043

(51) Int. Cl.
    *H04B 7/00* (2006.01)
(52) U.S. Cl. ........................ 455/41.2; 455/41.3; 375/259
(58) Field of Classification Search .................. 455/41.2; 375/259
    See application file for complete search history.

(56) References Cited

U.S. PATENT DOCUMENTS

| | | | | |
|---|---|---|---|---|
| 5,751,765 A | * | 5/1998 | Matsubara | 375/219 |
| 2007/0244388 A1 | * | 10/2007 | Sato et al. | 600/424 |
| 2010/0034436 A1 | | 2/2010 | Kono | |

FOREIGN PATENT DOCUMENTS

| | | |
|---|---|---|
| JP | 63-204806 | 8/1988 |
| JP | 01-209806 | 8/1989 |
| JP | 05-199268 | 8/1993 |
| JP | 05-327798 | 12/1993 |
| JP | 06-021981 | 1/1994 |
| JP | 08-241383 | 9/1996 |
| JP | 09-107242 | 4/1997 |
| JP | 11-017747 | 1/1999 |
| JP | 2002-141746 | 5/2002 |
| JP | 2009-200962 | 9/2009 |
| JP | 2009-261798 | 11/2009 |

OTHER PUBLICATIONS

International Search Report dated Nov. 2, 2010.

* cited by examiner

*Primary Examiner* — Temesgh Ghebretinsae
*Assistant Examiner* — David Bilodeau
(74) *Attorney, Agent, or Firm* — Scully, Scott, Murphy & Presser, P.C.

(57) ABSTRACT

A transmitting apparatus includes a receiving unit that receives an external specifying signal for specifying a center frequency of data to be transmitted; a control unit that outputs a specifying signal corresponding to the center frequency; and a frequency switching circuit. The frequency switching circuit includes a center frequency adjuster that adjusts a center frequency of a carrier wave that carries the data to be transmitted; a frequency modulator that modulates a frequency of the carrier wave according to the center frequency and the data to be transmitted; and a frequency switching unit that switches the center frequency of the carrier wave on the basis of the specifying signal.

7 Claims, 6 Drawing Sheets

TRANSMITTING APPARATUS, BODY-INSERTABLE APPARATUS, AND TRANSMITTING AND RECEIVING SYSTEM

CROSS-REFERENCE TO RELATED APPLICATIONS

This application is a continuation of PCT international application Ser. No. PCT/JP2010/063550 filed on Aug. 10, 2010 which designates the United States, incorporated herein by reference, and which claims the benefit of priority from Japanese Patent Application No. 2009-269043, filed on Nov. 26, 2009, incorporated herein by reference.

BACKGROUND OF THE INVENTION

1. Field of the Invention

The present invention relates to a frequency switching circuit that wirelessly transmits information to a receiving apparatus, a transmitting apparatus, a body-insertable apparatus, and a transmitting and receiving system.

2. Description of the Related Art

Conventionally, a capsule body-insertable apparatus wirelessly transmits information, which is acquired in-vivo by, for example, capturing images (hereinafter, in-vivo information), to a receiving apparatus that is carried by a subject. The receiving apparatus continuously waits for transmission of in-vivo information from the body-insertable apparatus. Each time upon receiving the in-vivo information, the receiving apparatus stores the received in-vivo information in, for example, a portable recording medium or transmits the in-vivo information almost in real time to a display device that is connected to the receiving apparatus via, for example, a network cable.

When information is wirelessly transmitted from the body-insertable apparatus to the receiving apparatus, the information to be transmitted is modulated at a predetermined frequency. In order to transmit information stably, it is necessary to obtain a stable modulated frequency. For example, Japanese Laid-open Patent Publication No. 09-107242 discloses, as a transmitting circuit for obtaining characteristics of stable modulated frequency, an FM modulation circuit including a first resistor that sets a modulation signal to a predetermined level and then inputs the modulation signal to an anode of a variable capacitance diode to control a center frequency; and a second resistor that applies a fixed bias voltage to a cathode of a modulation variable capacitance diode.

SUMMARY OF THE INVENTION

A transmitting apparatus according to an aspect of the present invention includes a receiving unit that receives an external specifying signal for specifying a center frequency of data to be transmitted; a control unit that outputs a specifying signal corresponding to the center frequency; and a frequency switching circuit. The frequency switching circuit includes a center frequency adjuster that adjusts a center frequency of a carrier wave that carries the data to be transmitted; a frequency modulator that modulates a frequency of the carrier wave according to the center frequency and the data to be transmitted; and a frequency switching unit that switches the center frequency of the carrier wave on the basis of the specifying signal.

A body-insertable apparatus according to another aspect of the present invention includes a receiving unit that receives an external specifying signal for specifying a center frequency of data to be transmitted; a control unit that outputs the specifying signal corresponding to the center frequency; and a frequency switching circuit. The frequency switching circuit includes a center frequency adjuster that adjusts a center frequency of a carrier wave that carries the data to be transmitted; a frequency modulator that modulates a frequency of the carrier wave according to the center frequency and the data to be transmitted; and a frequency switching unit that switches the center frequency of the carrier wave on the basis of the specifying signal.

A transmitting and receiving system according to still another aspect of the present invention includes the transmitting apparatus according to the invention; and a receiving apparatus that receives the data by using a plurality of antennas.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Best modes for carrying out the present invention will be described in detail below with the accompanying drawings. The following embodiments do not limit the present invention. In the following descriptions, each diagram only schematically shows the shape, size, and positional relationship such that the content of the present invention can be understood. Thus, the present invention is not limited to only the shape, size, and positional relationship illustrated in each diagram.

A configuration and operations of an in-vivo information acquiring system 1 according to an embodiment of the present invention will be described in detail below using the drawings. In the embodiment, a case will be taken as an example in which a capsule medical apparatus 10 acting as a body-insertable apparatus is used that is perorally inserted into a subject 100 and acquires in-vivo information on the subject while moving from the esophagus to the anus of the subject 100. However, the present invention is not limited to this. Various body-insertable apparatuses can be used, such as a capsule medical apparatus that acquires some sort of in-vivo information on the subject 100 while being in various internal organs, such as the stomach and the intestine of the subject 100. In the present embodiment, images (in-vivo images) acquired by capturing images using an imaging unit 15, which will be described below, are taken as an example of in-vivo information that the capsule medical apparatus 10 acquires. However, the present invention is not limited to this. Various types of information, such as the in-vivo temperature, pressure, pH value of the subject, may be used as the subject in-vivo information.

Figure 1:
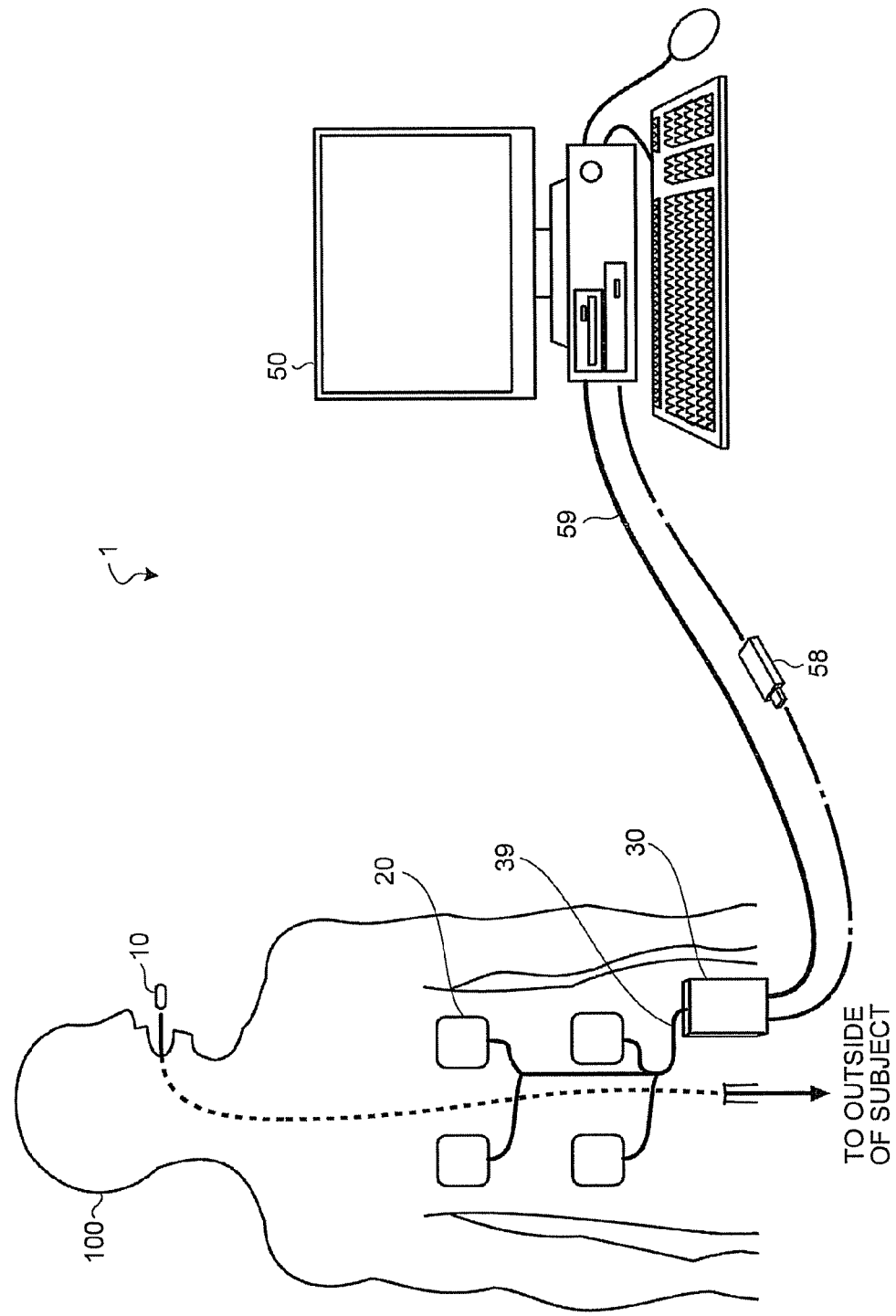
FIG. 1 is a schematic diagram of a schematic configuration of an in-vivo information acquiring system according to an embodiment of the present invention.

FIG. 1 is a schematic diagram of a schematic configuration of the in-vivo information acquiring system 1 according to the embodiment of the present invention. As illustrated in FIG. 1, the in-vivo information acquiring system 1 acting as a transmitting and receiving system includes the capsule medical apparatus 10 sized such that it can be swallowed by the subject 100; a receiving apparatus 30 that can receive image data transmitted as radio signals from the capsule medical apparatus 10; and an information processing apparatus 50 to which data can be input from the receiving apparatus 30 or from which data can be output to the receiving apparatus 30 via a wired interface such as a wired interface using a communication cable 59 such as a universal serial bus (USB) cable; via a wireless interface such as a Bluetooth (registered trademark) device; or via a portable recording medium 58 such as a flash memory.

An external antenna 20 is connected to the receiving apparatus 30 via a connection cable 39 or a balun (not illustrated). Radio signals that are transmitted from the capsule medical apparatus 10 are input to the receiving apparatus 30 via the external antenna 20.

The capsule medical apparatus 10 acquires subject in-vivo images, for example, constantly and transmits the image data to the receiving apparatus 30 every time it acquires subject in-vivo images. Thus, when the receiving apparatus 30 and the information processing apparatus 50 are configured such that they are connected via a wired interface or a wireless interface and subject in-vivo images received by the receiving apparatus 30 are input to the information processing apparatus 50 as needed, the information processing apparatus 50 can display in real time subject in-vivo images acquired by the capsule medical apparatus 10. For example, in the case where the cycle in which the capsule medical apparatus 10 acquires images is two frames per second, the information processing apparatus 50 acquires image data from the receiving apparatus 30 at at least two cycles per second and displays the image data. Accordingly, subject in-vivo images are displayed to the user in almost real time.

Figure 2:
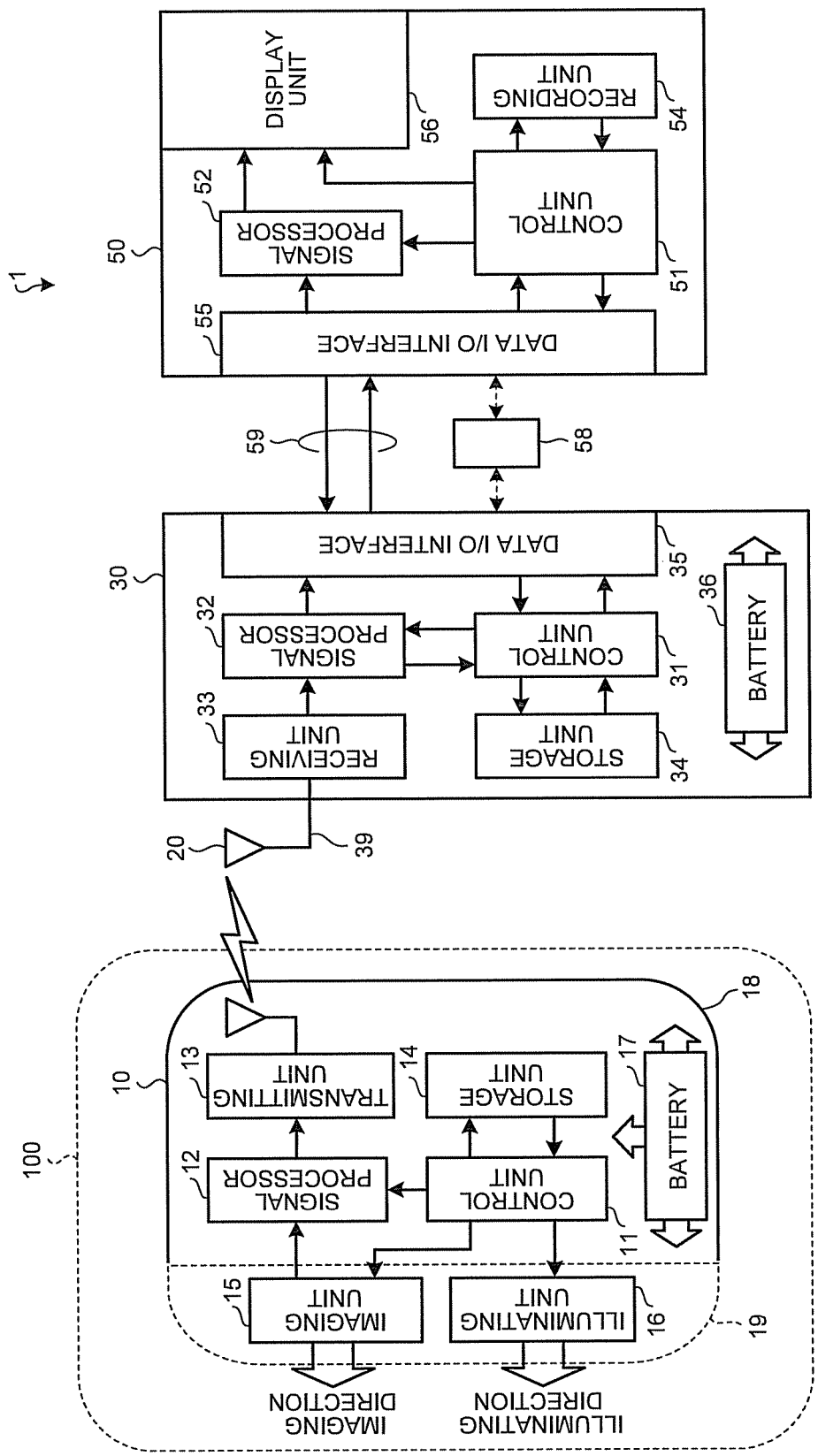
FIG. 2 is a block diagram of a schematic configuration of each apparatus that constitutes the in-vivo information acquiring system according to the embodiment of the present invention.

The in-vivo information acquiring system 1 according to the present embodiment will be described in detail below using the block diagram of FIG. 2. FIG. 2 is a block diagram of a schematic configuration of each apparatus constituting the in-vivo information acquiring system 1 according to the present embodiment.

As illustrated in FIG. 2, the capsule medical apparatus 10 that is inserted into the subject 100 includes the imaging unit 15 that acquires in-vivo images of the subject 100; an illuminating unit 16 that illuminates in-vivo the subject 100 when the imaging unit 15 captures images; a signal processor 12 that performs predetermined processing on the data of in-vivo images acquired by the imaging unit 15 (hereinafter, "image data"); a transmitting unit 13 that serves as a transmitting apparatus that transmits image data processed by the signal processor 12 to the receiving apparatus 30; a control unit 11 that controls each unit of the capsule medical apparatus 10; a storage unit 14 that stores various programs for the control unit 11 to control each unit and various types of setting data; and a battery 17 that supplies power to each unit of the capsule medical apparatus 10. The battery 17 includes a power supply circuit (not illustrated).

Each unit of the capsule medical apparatus 10 is housed in a capsule housing (casing) that includes a housing 18 that is approximately cylindrical or ellipsoidal with a semi-spherical and dome-shaped one end and an open other end; and a semi-spherical cap 19 that is fitted to the opening of the housing 18 so the housing 18 is sealed watertight. The capsule-shaped housing (18, 19) is sized such that, for example, it can be swallowed by the subject 100. In the present embodiment, at least the cap 19 is formed of a transparent material, and a circuit substrate on which the imaging unit 15 and the illuminating unit 16 are mounted is arranged in the capsule housing (18, 19) and on the side of the cap 19. The imaging direction of the imaging unit 15 and the illuminating direction of the illuminating unit 16 face the outside of the capsule medical apparatus 10 via the cap 19. Thus, while the illuminating unit 16 illuminates in-vivo the subject 100, the imaging unit 15 can capture in-vivo images of the subject 100.

In the present embodiment, the capsule medical apparatus 10 that includes a pair of the imaging unit 15 and the illuminating unit 16 is taken as an example. However, the present invention is not limited to this. For example, a capsule medical apparatus including multiple pairs of an imaging unit and an illuminating unit, i.e., a pantoscopic capsule medical apparatus, may be used. For example, in a pantoscopic capsule medical apparatus, the housing 18 is hollow and cylindrical with openings at both ends, and the caps 19, which are transparent, are fitted to the openings. An imaging unit and an illuminating unit are provided to each of the openings such that the imaging units face the outside of the capsule medical apparatus via the caps 19.

The configuration of the receiving apparatus 30 according to the present embodiment will be described in detail using FIG. 2. As illustrated in FIG. 2, the receiving apparatus 30 that is arranged outside the subject 100 (for example, on the surface of the subject 100 or on the clothes that the subject 100 wears) includes a receiving unit 33 that receives image data that is transmitted from the capsule medical apparatus 10; a signal processor 32 that performs predetermined processing on the received image data; a control unit 31 that controls each unit of the receiving apparatus 30; a storage unit 34 that stores various programs for the control unit 31 to control each unit and various types of setting data; a data I/O interface 35 that functions as an interface in communications with the information processing apparatus 50, which will be described below; and a battery 36 that supplies power to each unit of the receiving apparatus 30.

Each unit of the receiving apparatus 30 is housed in a casing sized such that it can be carried by the subject 100, such as a human. Because a power supply unit including the battery 36 is installed in the casing as described above, the receiving apparatus 30 according to the present embodiment does not need a power supply cable and thus can be carried by the subject 100.

The configuration of the information processing apparatus 50 according to the embodiment will be described in detail below using FIG. 2. The information processing apparatus 50 according to the present embodiment is configured by using an information processing apparatus having a computing function, such as a personal computer, and a display function. As illustrated in FIG. 2, the information processing apparatus 50 includes a data I/O interface 55 that functions as an interface in communications with the receiving apparatus 30; a signal processor 52 that performs predetermined processing on the image data, which is input via the data I/O interface 55, and generates image signals for a display; a display unit 56 that displays subject in-vivo images according to image signals that are input by the signal processor 52; a control unit 51 that controls each unit of the information processing apparatus 50 and performs various arithmetic operations; and a recording unit 54 that stores programs in which various operations to be executed by the control unit 51 are described and various types of setting data.

Figure 3:
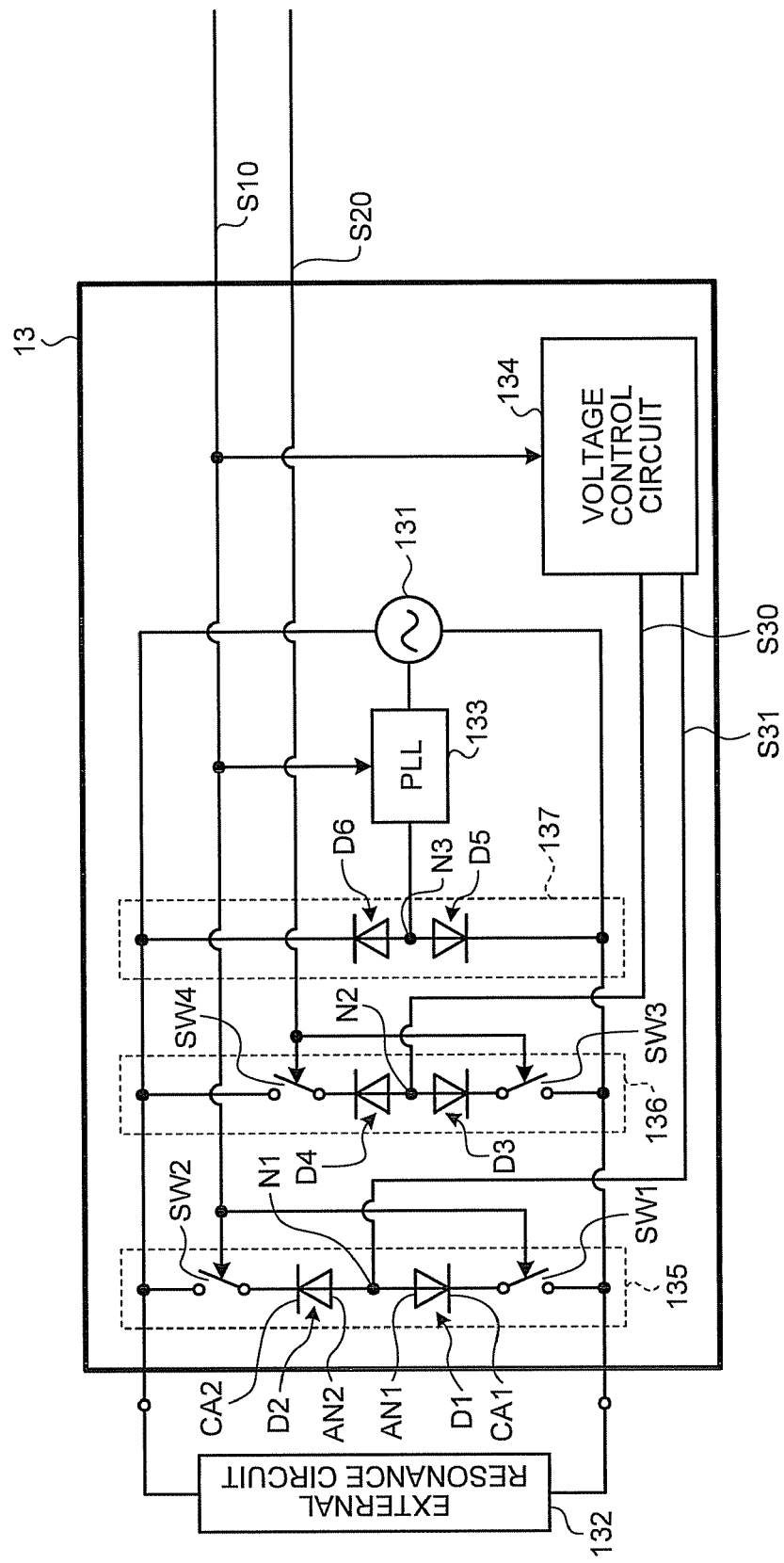
FIG. 3 is a circuit diagram of a schematic configuration of a transmitting unit of a capsule medical apparatus according to the embodiment of the present invention.

Signal processing performed by the capsule medical apparatus 10 acting as a transmitting apparatus when performing a radio transmission to the receiving apparatus 30 will be described with reference to FIG. 3. FIG. 3 is a circuit diagram of a schematic configuration of a circuit constituting the transmitting unit 13 of the capsule medical apparatus 10 according to the embodiment of the present invention. The transmitting unit 13 includes a center frequency adjuster 137 that is connected in parallel with a reference frequency oscillator circuit 131 and an external resonance circuit 132; a frequency switching unit 135; and a frequency modulator 136. The center frequency adjuster 137 is connected to the reference frequency oscillator circuit 131 via a PLL (phase-locked loop) 133. The frequency switching unit 135 and the frequency modulator 136 are connected to a voltage control circuit 134 acting as a voltage control unit that controls the voltage to finely adjust the frequency.

The center frequency adjuster 137 includes variable capacitance diodes D5 and D6 and adjusts the center frequency of a carrier frequency according to the voltage applied, via the PLL 133 and from the reference frequency oscillator circuit 131, to a connecting point N3 that is connected between the anodes. The PLL 133 switches the carrier frequency in response to an input of a frequency switch signal S10. The PLL 133 locks the phase according to a clock and thus synchronizes the phase of the reference clock at the rising edge (or the trailing edge) of the clock, thereby stably oscillating the carrier wave and reducing frequency variations. The reference frequency oscillator circuit 131 is configured by using a crystal oscillator that oscillates at an approximately predetermined frequency with respect to, for example, an applied voltage.

The frequency modulator 136 includes variable capacitance diodes D3 and D4 and switches SW3 and SW4. The frequency modulator 136 turns on the switches SW3 and SW4 in response to an input of a data switch signal S20, which is output from the control unit 11, so that the carrier wave frequency is modulated at a frequency corresponding to the input data signal. The frequency modulator 136 is connected to the voltage control circuit 134 at a connecting point N2 between the anodes of the variable capacitance diodes D3 and D4. The voltage control circuit 134 outputs a capacitance switch signal S30, varies the capacitances of the variable capacitance diodes D3 and D4 by controlling the voltage applied to them, and thus finely adjusts the resonance frequency of the resonance circuit including the external resonance circuit 132.

The frequency switching unit 135 includes variable capacitance diodes D1 and D2 and switches SW1 and SW2. When the center frequency of a radio signal to be transmitted is, for example, equal to or less than 30 MHz, the frequency switch signal S10 that is output from the control unit 11 turns on the switches SW1 and SW2, thereby switching the frequency to be equal to or less than 30 MHz. The voltage control circuit 134 outputs a capacitance switch signal S31 based on the input frequency switch signal S10, varies the capacitances of the variable capacitance diodes D1 and D2 by controlling the voltage to be applied to them, and thus finely adjusts the resonance frequency of the resonance circuit including the external resonance circuit 132. The capacitance switch signal S31 is input to the variable capacitance diodes D1 and D2 at a connecting point N1 between anodes AN1 and AN2 of the variable capacitance diodes D1 and D2, and the switches SW1 and SW2 are arranged on the side of the cathodes CA1 and CA2.

In other words, the carrier frequency is adjusted by the center frequency adjuster 137, modulated by the frequency modulator 136 at a frequency corresponding to a data signal that is input by the frequency modulator 136, and then transmitted as a radio signal to the receiving apparatus 30 via the external resonance circuit 132. When the frequency of a radio signal received by the receiving apparatus 30 is, for example, less than 30 MHz, the radio signal can be transmitted to the receiving apparatus 30 by switching the frequency of the radio signal using the frequency switching unit 135.

Figure 4:
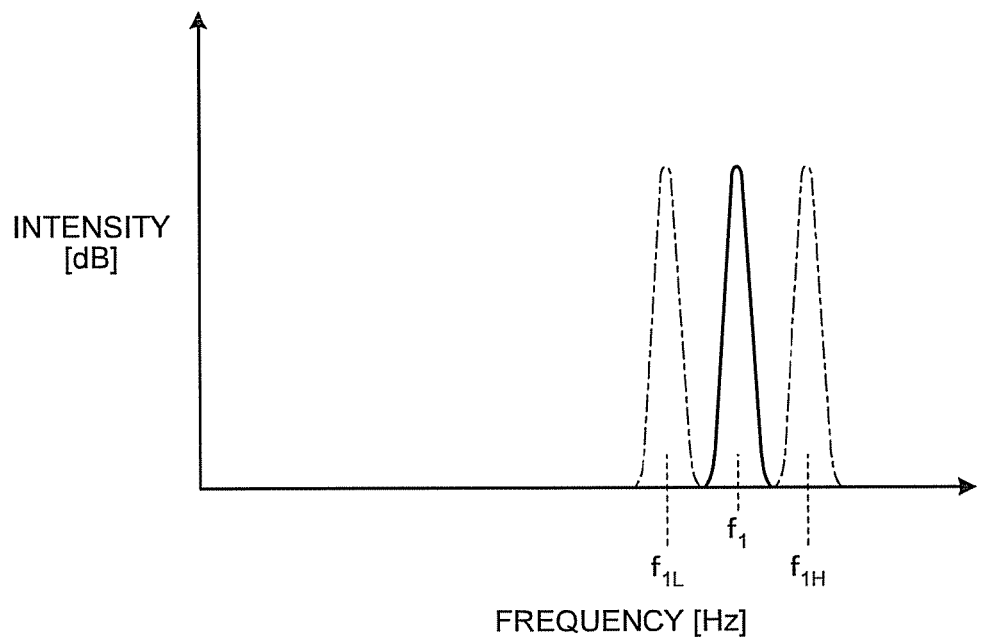
FIG. 4 is a graph of an example of intensity-frequency characteristics according to the embodiment of the present invention.
Figure 5:
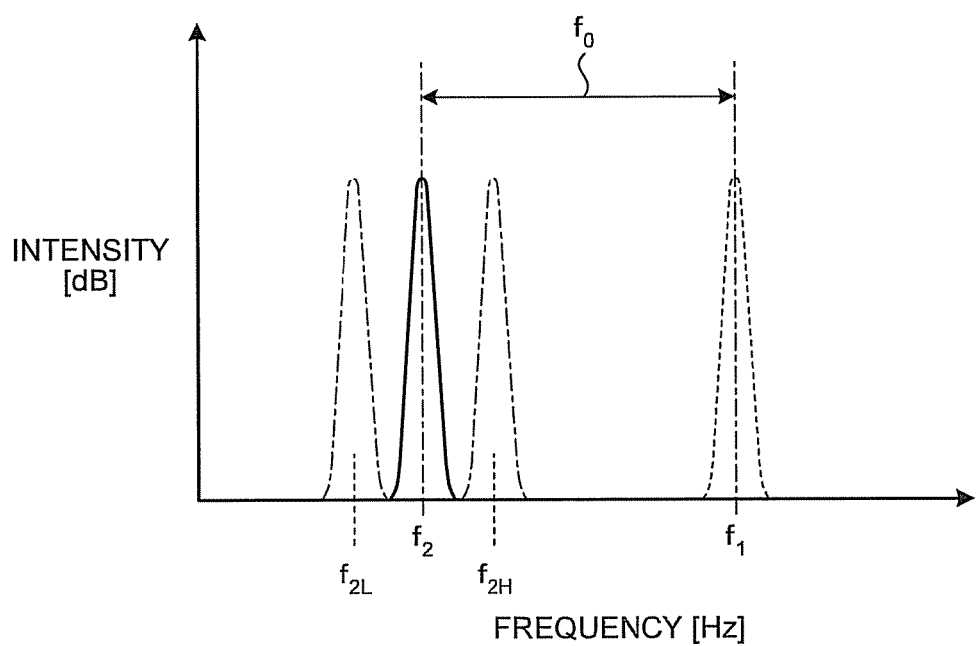
FIG. 5 is a graph of an example of intensity-frequency characteristics according to the embodiment of the present invention.

The switch of the center frequency performed by the frequency switching unit 135 will be described below with reference to FIGS. 4 and 5. FIGS. 4 and 5 are graphs of examples of intensity-frequency characteristics according to the embodiment of the present invention. FIG. 4 is a graph of intensity-frequency characteristics before a frequency switch performed by the frequency switching unit 135, and FIG. 5 is a graph of intensity-frequency characteristics after a frequency switch performed by the frequency switching unit 135.

As illustrated in FIG. 4, when the switches SW1 and SW2 of the frequency switching unit 135 are off, the frequency $f_1$ that is output from the external resonance circuit 132 has a peak at, for example, 80 MHz. When the switches SW1 and SW2 are off, a fine adjustment of a few tens of MHz can be made for frequencies $f_{1L}$ to $f_{1H}$, for example, for the frequency $f_1$ by controlling the voltage, which is to be applied, by using the voltage control circuit 134.

In contrast, when the switches SW1 and SW2 of the frequency switching unit 135 are on, the peak shifts to a center frequency $f_2$, for example, 30 MHz as illustrated in FIG. 5. The difference $f_0$ between the two center frequencies $f_1$ and $f_2$ is 50 MHz. The configuration of the present embodiment makes it easy to switch the frequency greatly. When the switches SW1 and SW2 are on, a fine adjustment of a few tens of MHz can be made for frequencies $f_{2L}$ to $f_{2H}$, for example, for a frequency $f_2$ by controlling the voltage, which is to be applied, by using the voltage control circuit 134.

Figure 6:
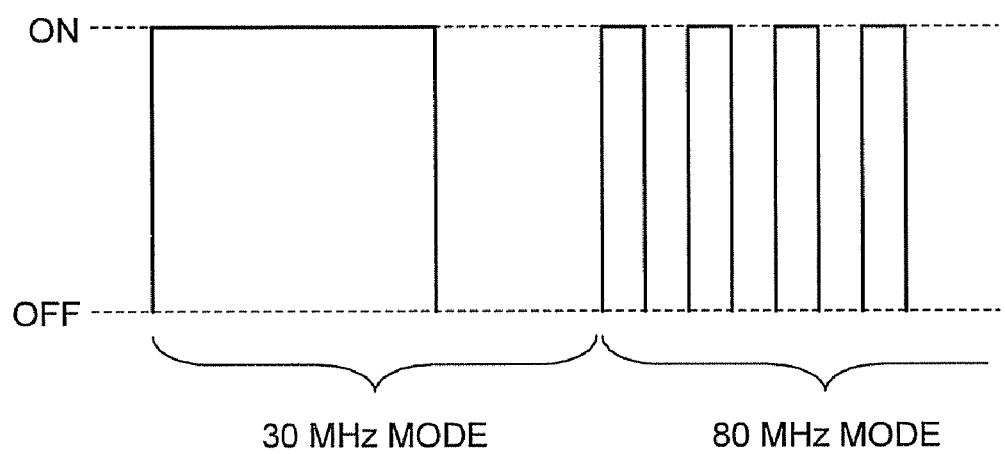
FIG. 6 is a timing chart of an example of the center frequency on/off, when the capsule medical apparatus according to the embodiment of the present invention is started.

When the power of the capsule medical apparatus 10 is turned on, the control unit 11 may confirm the frequency of a radio signal to be transmitted to the receiving apparatus 30 and, depending on the frequency, may cause the illuminating unit 16 to light up or blink for a few seconds. FIG. 6 is a timing chart of an example of the illuminating unit 16 on/off depending on the center frequency, when the capsule medical apparatus according to the embodiment of the preset invention is started. For example, in a case where the center frequency is alternately set to a 30 MHz mode and a 80 MHz mode each time when the capsule medical apparatus 10 is restarted, when the frequency is 30 MHz, the illuminating unit 16 lights up for about five seconds. Thereafter, when the capsule medical apparatus 10 is restarted and thus the center frequency is set to 80 MHz, the illuminating unit 16 blinks for about five seconds (repetition of on/off of illumination). This allows the user to confirm the frequency of a radio signal, which is to be transmitted from the capsule medical apparatus 10, prior to insertion of the capsule medical apparatus 10 into the subject 100.

The frequency does not need to be changed each time the capsule medical apparatus 10 is restarted. A frequency mode may be set according to a frequency setting signal from the receiving apparatus 30. A display unit including LEDs may be provided for the receiving apparatus 30 and the LEDs may be made to light up or blink as described above. The display unit may be provided with a screen on which a message can be displayed, or a message may be displayed on the display unit 56 of the information processing apparatus 50.

Figure 7:
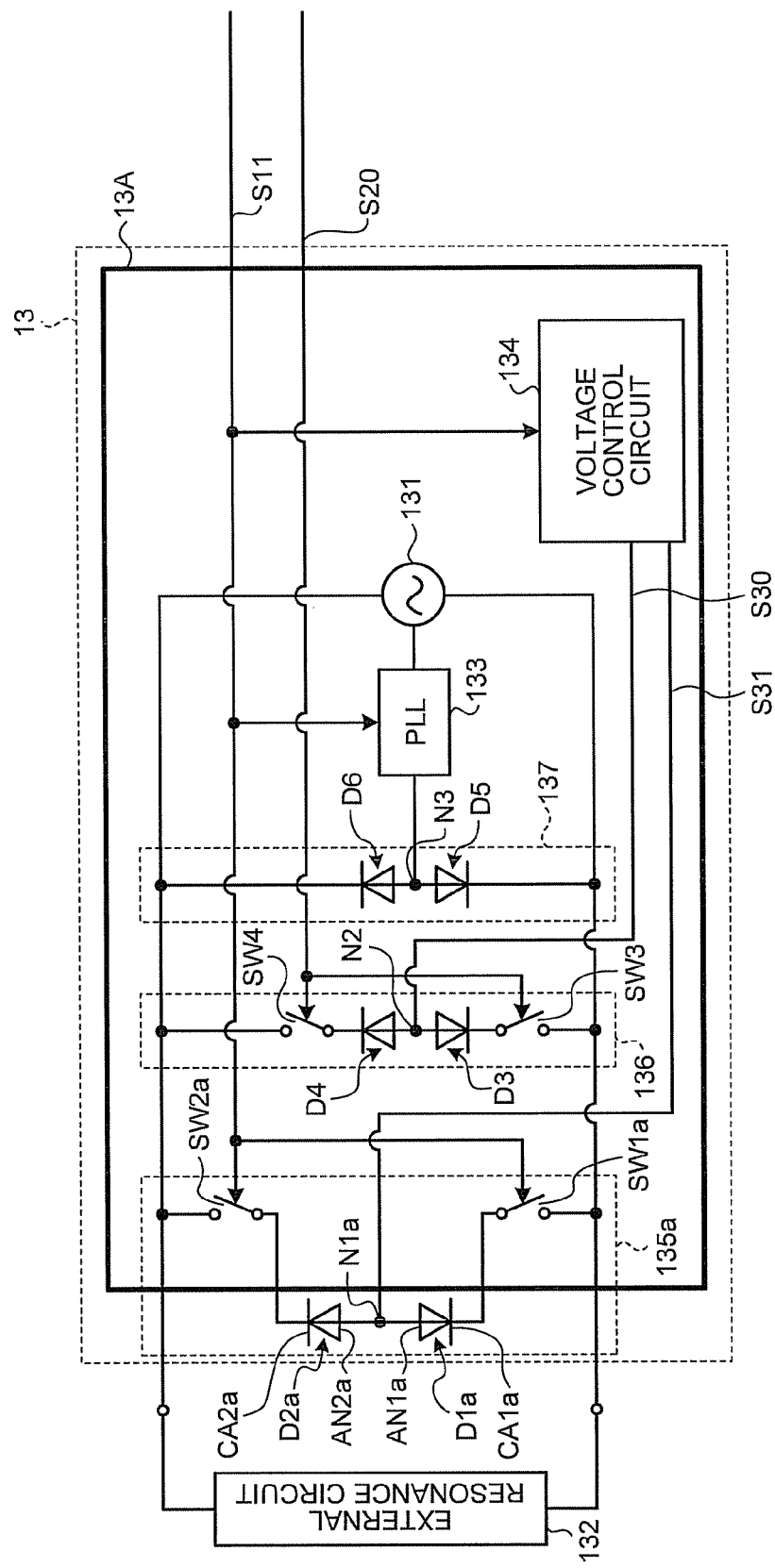
FIG. 7 is a circuit diagram of a schematic configuration of a modification of a transmitting unit according to the embodiment of the present invention.

The variable capacitance diodes of the frequency switching unit may be provided to the outside of the circuit. FIG. 7 is a circuit diagram of a schematic configuration of a circuit of a modification of the transmitting unit 13 according to the embodiment of the present invention. The configuration of the modification illustrated in FIG. 7 is different from that of FIG. 3 in that variable capacitance diodes D1$a$ and D2$a$ of a frequency switching unit 135$a$ are arranged outside a transmitting circuit 13A. Regarding the operations, like those of the configuration in FIG. 3, the frequency of a radio signal to be transmitted is switched by switching on/off the switches SW1$a$ and SW2$a$ connected to cathodes CA1$a$ and CA2$a$, outside the transmitting circuit 13A, according to a frequency switch signal S11.

The voltage control circuit 134 outputs a capacitance switch signal S31 to a connecting point N1$a$ between anodes AN1$a$ and AN2$a$ of the variable capacitance diodes D1$a$ and D2$a$ and thus controls the voltage, thereby finely adjusting the capacitance.

In the configuration of the modification of FIG. 7, the variable capacitance diodes are externally provided. This increases the degree of freedom of the variable capacitance diodes D1$a$ and D2$a$. Especially, even when the area in which the variable capacitance diodes are arranged in the transmitting circuit 13A is made small for a size reduction, preferable variable capacitance diodes can be arranged outside, which further makes a switch to a different frequency easy.

In the above-described embodiment, the single capsule medical apparatus can transmit radio signals of multiple center frequencies to the receiving apparatus. In addition, the voltage control circuit can perform a fine adjustment of the frequency by using the voltage control circuit, and thus more accurate signals can be transmitted. In the present embodiment, the variable capacitance diodes may be configured with capacitance circuits.

As described above, the frequency switching circuit, the transmitting apparatus, the body-insertable apparatus, and the transmitting and receiving system are useful, for example, when a transmitting apparatus transmits data to a receiving apparatus that uses different frequencies. They are especially suitable for a body-insertable apparatus that is inserted into a subject, captures in-vivo images of the subject, and transmits the in-vivo images as radio signals to a receiving apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A transmitting apparatus that has a capsule-shaped casing and transmits data, comprising:
   a receiving unit that receives an external specifying signal from the outside of the casing for specifying a center frequency of data to be transmitted;
   a control unit that outputs a specifying signal corresponding to the center frequency;
   a frequency switching circuit that includes
      a center frequency adjuster that adjusts a center frequency of a carrier wave that carries the data to be transmitted;
      a frequency modulator that modulates a frequency of the carrier wave according to the center frequency and the data to be transmitted; and
      a frequency switching unit, of which a variable capacitance unit is connected in parallel to an external resonance circuit that oscillates the carrier wave, that switches the center frequency of the carrier wave on the basis of the specifying signal; and
   a voltage control unit that controls voltage applied to the variable capacitance unit on the basis of the specifying signal to vary the capacitance and finely adjusts a resonance frequency of the external resonance circuit.

2. The transmitting apparatus according to claim 1, wherein a difference between the frequency before being switched by the frequency switching unit and the frequency after being switched by the frequency switching unit is equal to or more than 50 MHz.

3. The transmitting apparatus according to claim 1, wherein, in the frequency switching unit, the variable capacitance unit includes
   two variable capacitance diodes whose anodes are connected to each other; and
   a switch that switches power on/off to the variable capacitance diodes.

4. The transmitting apparatus according to claim 3, wherein the voltage control unit supplies, between the anodes, a voltage for finely adjusting a resonance frequency of the external resonance circuit.

5. A body-insertable apparatus that has a capsule-shaped casing and transmits data, comprising:
   a receiving unit that receives an external specifying signal from the outside of the casing for specifying a center frequency of data to be transmitted;
   a control unit that outputs the specifying signal corresponding to the center frequency;
   a frequency switching circuit that includes
      a center frequency adjuster that adjusts a center frequency of a carrier wave that carries the data to be transmitted;
      a frequency modulator that modulates a frequency of the carrier wave according to the center frequency and the data to be transmitted; and
      a frequency switching unit, of which a variable capacitance unit is connected in parallel to an external resonance circuit that oscillates the carrier wave, that switches the center frequency of the carrier wave on the basis of the specifying signal; and
   a voltage control unit that controls voltage applied to the variable capacitance unit on the basis of the specifying signal to vary the capacitance and finely adjusts a resonance frequency of the external resonance circuit.

6. The body-insertable apparatus according to claim 5, further comprising:
   an imaging unit that captures an in-vivo image of a subject; and
   an illuminating unit that illuminates a region where the image is captured with light when the imaging unit captures the image,
   wherein the illuminating unit lights up or blinks depending on a set frequency when power of the body-insertable apparatus is turned on.

7. A transmitting and receiving system comprising:
   the transmitting apparatus according to claim 1; and
   a receiving apparatus that receives the data by using a plurality of antennas.

* * * * *